United States Patent [19]

Clancy

[11] Patent Number: 4,873,090
[45] Date of Patent: Oct. 10, 1989

[54] NON-ADJUVENATED VACCINE

[75] Inventor: Robert L. Clancy, Newcastle, Australia

[73] Assignee: Broncostat Pty. Limited, Perth, Australia

[21] Appl. No.: 2,625

[22] PCT Filed: Mar. 17, 1986

[86] PCT No.: PCT/AU86/00071

§ 371 Date: Nov. 12, 1986

§ 102(e) Date: Nov. 12, 1986

[87] PCT Pub. No.: WO86/05691

PCT Pub. Date: Oct. 9, 1986

[30] Foreign Application Priority Data

Mar. 27, 1985 [AU] Australia ............................. PG9928

[51] Int. Cl.$^4$ .................. A61K 9/48; A61K 39/02
[52] U.S. Cl. ...................................... 424/451; 424/92; 424/436; 424/475; 424/480; 424/489; 424/499
[58] Field of Search .............. 435/851, 883, 875, 885; 424/92, 451, 436, 489, 499, 475, 480

[56] References Cited

U.S. PATENT DOCUMENTS

| | | | |
|---|---|---|---|
| 3,855,197 | 12/1974 | Hirsch et al. | 435/851 X |
| 3,990,947 | 11/1976 | Butler et al. | 435/883 X |
| 4,071,412 | 1/1978 | Eisenberg et al. | 435/875 X |
| 4,337,314 | 6/1982 | Deschger et al. | 435/253 |
| 4,407,949 | 10/1983 | Kniskern et al. | 435/101 |
| 4,455,142 | 6/1984 | Martins et al. | 424/92 X |
| 4,460,575 | 7/1984 | d'Hinterland et al. | 424/92 |
| 4,575,459 | 3/1986 | Homma et al. | 424/87 |

FOREIGN PATENT DOCUMENTS 0899399 6/1962 United Kingdom ................ 435/875

OTHER PUBLICATIONS

Infection and Immunity, vol. 39, No. 2, Feb. 1983, pp. 491–496 R. L. Clancy et al. "Specific Immune Response in the Respiratory Tract after Administration of an Oral Polyvalent Bacterial Vaccine", whole document.
Biological Abstracts, vol. 65, No. 2, 1978, no. 894, ref. 9268 J. R. Gerke et al.: "Oral Vaccination and Multivalent Vaccine Against Psuedomonas aeruginosa keratitis" & Invest. Ophthalmol. Vis. Sci, 16(1), 76–80, 1977–Abstract.
Biological Abstracts/RRM, No. 23043018, J. Seifert et al.: "Oral Application of Bacterial Vaccine for Infection Prophylaxis" & Chir. Forum Exp. Klin. Forsch. (DE), 1980, vol. o. No. 0, pp. 73–78, Title and terms.

Primary Examiner—Thurman K. Page
Attorney, Agent, or Firm—Ladas & Parry

[57] ABSTRACT

An enteral non-adjuvenated monobacterial vaccine comprising killed bacteria gives a better protection against acute episodes of infection in patients with long term chronic lung disease than a conventional adjuvenated polybacterial vaccine. The bacteria are usually *Haemophilus influenza, Streptococcus pneumoniae, Pseudomonas aeruginosa* or *Staphylococcus aureus*.

11 Claims, No Drawings

NON-ADJUVENATED VACCINE

TECHNICAL FIELD

The present invention relates to an enteral monobacterial vaccine comprising killed *Haemophilus influenza* or *Streptococcus pneumoniae*, a process for the manufacture of such a vaccine and a method of preventing acute mucosal infections in humans having chronic mucosal disease by administering such a vaccine.

BACKGROUND ART

Acute episodes of bronchitis in cigarette smokers are a major health problem and are in particular a cause of morbidity and mortality with patients with chronic obstructive lung disease (COLD). The upper respiratory tract of these patients is commonly colonised with *Haemophilus influenzae* and/or *Streptococcus pneumoniae*, and it has been held that a shift in the shot-bacteria balance favouring infection with these organisms is the immediate cause of acute bronchitis. Children with cystic fibrosis commonly suffer from chronic infection by *Pseudomonas aeruginosa* and *Staphylococcus aureus*. Polybacterial vaccines containing a selection of killed bacteria normally associated with infection of the respiratory tract have been available for many years. The polybacterial vaccines contain an adjuvant of conventional type whose function according to established methodology is to enhance the response of the patient to the antigen thereby leading to enhanced immunity. The adjuvant may be a chemical agent. Alternatively, the variety of organisms themselves function in a non-specific way to activate the immune system. Such adjuvant-containing polybacterial vaccine has been commercially available in tablet form for oral digestion. The tablets are enteric coated to allow passage through the stomach, followed by stimulation of gut-associated lymphoid tissue. However, the effectiveness of these polybacterial vaccines has been disappointing in the treatment of acute bacterial infections of the respiratory tract in humans having chronic mucosal inflammations.

It is an object of the present invention to provide an enteral vaccine against infections of mucosal surfaces in humans having long term mucosal disease.

DISCLOSURE OF INVENTION

In a first aspect, the present invention provides an enteral monobacterial vaccine comprising killed bacteria for immunisation against bacterial infection of mucosal sites. Examples for such bacteria are *Haemophilus influenzae*. *Streptococcus pneumoniae, Pseudomonas aeruginosa* and *Staphylococcus aureus*. Preferred is a vaccine comprising killed *Haemophilus influenzae*. A particular aspect of the vaccine of the present invention is that no adjuvant is added to the killed bacteria, i.e. that the vaccine stimulates only a limited antigenic response. Adjuvants usually added to vaccines and absent in the vaccine of the present invention are killed bacteria known to illicit a strong antigenic response, e.g. killed *Mycobacterium tuberculosis* such as *Bacillus Calmette-Guerin* (BCG), or killed *Corynebacterium parvum*, a selection of closely related bacteria, whereby each species acts as an adjuvant for the other bacteria, or inorganic polymeric material, e.g. aluminium oxide or aluminum phosphate, which is useful especially in parenteral vaccines.

The enteric vaccine may be in the form of tablets, especially enteric coated tablets, granules, capsules or dragees for oral administration, or provided e.g. as suppositories for rectal administration. The dosage unit form may contain from approximately $10^9$ bacteria to approximately $10^{13}$ bacteria, preferably from approximately $10^{10}$ bacteria to approximately $10^{12}$ bacteria, together with suitable carriers of organic or inorganic nature.

Suitable carries are especially fillers, such as sugars, for example lactose, saccharose, mannitol or sorbitol, cellulose preparations and/or calcium phosphates, for example tricalcium phosphate or calcium hydrogen phosphate, amino acids, for example glycine, also binders, such as starch pastes using, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol, further choleretic agents, e.g. sodium taurocholate, sodium tauroglycocholate or ox bile. Dragee cores are provided with suitable coatings that may be resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as acetylcellulose phthalate or hydroxypropylmethylcellulose phthalate. Dyes or pigments can be added to the tablets or dragee coatings, for example for identification purposes or to indicate different doses of active ingredient. Compounds illiciting an antigenic response, i.e. adjuvants, are excluded as carriers or adjuncts in the vaccine of the invention.

In a second aspect, the present invention relates to processes known per se for the manufacture of the inventive vaccine, characterised in that the bacteria are cultured, then killed, lyophilised and/or dried, mixed with carriers, fillers and adjuncts, and brought into the form of a therapeutically applicable enteric pharmaceutical composition.

Such processes for the manufacture of vaccines are known in the art. The bacteria may be grown on plates, e.g. agar plates containing various nutrients, for example blood or "chocolate" agar plates, or in suspension in fermentation broth containing nutrients in dissolved form, e.g. milk hydrolysates, lactalbumin hydrolysates, corn steep liquors, glucose, starches, tryptic soy broth and the like, and growth stimulating substances, e.g. hormones and coenzymes, also in the form of serum dilutions, for example of horse serum or fetal calf serum. The cultures must be kept under strictly aseptic conditions, and optionally small amounts of antibiotics, e.g. bacitracin, are added to prevent overgrow by unwanted bacteria.

The organisms are killed for example with formalin, phenol or ether, optionally homogenised and washed extensively. Sterility of the killed bacteria has to be tested carefully, e.g. by inoculation into a medium or an agar plate known to allow rapid growth of viable bacteria. Pharmaceutical preparations for oral or rectal administration are obtained from the killed bacteria by conventional lyophilising, drying, mixing, granulating and/or confectioning processes under sterile conditions.

In a third aspect, the invention relates also to a method of preventing acute mucosal infections in humans having chronic mucosal disease, characterised in that a vaccine of the invention is administered to a patient in need thereof. Preferably one to three unit doses of the vaccine containing $10^{10}$ to $10^{12}$ killed bacteria are administered for two to five consecutive days. More than one course may be required, and three courses at approximately three to five weeks intervals are preferred.

The invention is applicable to patients having long term diseases of mucosal sites, e.g. of the respiratory tract, eye, urogenital system and the gut. These mucosal sites form part of a common mucosal system linked by an intermucosal cell traffic. Certain infections are restricted to mucosal sites and are thus not susceptible to antibodies in the bloodstream. In the present invention the antigen is administered enterally, i.e. to the gut, and activated cells then circulate through the blood to lodge at distant mucosal sites, where they secrete their antibody on the mucosal surface or act directly on it.

The vaccine of the present invention is particularly effective to provide immunity against acute bacterial infections of the respiratory tract, especially of the bronchi, under circumstances of chronic inflammation. Long term lung diseases are prevalent in patients who are smokers or ex-smokers. This may include patients with chronic lung diseases, such as chronic bronchitis and other diseases associated with smoking, and children suffering from cystic fibrosis-related lung diseases.

Surprisingly, it appears that the immunisation efficacy of the vaccine arises from the absence of adjuvants, which would normally be included in such a vaccine formulation to promote the protective effect. The reason for this is not well understood, but may derive from the delicate balance which exists within the mucosa between suppressor and helper mechanisms in the production of immunity. The production of antibodies by B-cells is regulated by T-cells comprising helper and suppressor cells, though their exact functioning in the mucosal system is not understood. In patients with chronical inflamed bronchi (e.g. chronic bronchitis) there may be a dominance of suppressor T-cells such that the stimulation effect or the adjuvant is to produce a net suppression (rather than the intended activation) of the immune system. In the absence of adjuvant, a limited response occurs which is insufficient to trigger the suppressor mechanism. This is merely a hypothesis, but it is surprisingly found that for patients with chronic bronchitis, addition of extra bacteria to the H. influenzae vaccine creates a vaccine which fails to protect against acute bronchitis.

EXEMPLARY MODE OF CARRYING OUT INVENTION

The efficacy of the vaccine of the invention is shown by the results of a double-blind, prospective, placebo-controlled trial on sixtyseven patients with established chronic obstructive lung disease. No patient was taking steroids or immunosuppressive agents, but many took bronchodilator drugs and antibiotics as necessary.

Four groups were tested: Two placebo groups, one took glucose tablets, the second enteric coated tablets compounded in an identical fashion to the monobacterial vaccine of the invention and the state of the art polybacterial vaccine. The third group took a killed polybacterial vaccine representing the nearest state of the art and known to be effective in the prophylaxis of bacterial infections of the respiratory tract in normal, healthy humans. Each enteric coated tablet containing $1.5 \times 10^9$ H. influenzae, $10^9$ Staphylococcus aureus, $10^9$ of each of S. pneumoniae types I, II and III, $10^9$ Streptococcus, and 25 mg Fel Bovis sicc. (ox bile). These tablets are produced by Swiss Serum (Berne), and sold as Buccalin Berna ®. The fourth group took a vaccine of the invention, namely enteric coated tablets each containing $10^{11}$ killed H. influenzae as described in the accompanying Example.

At zero times, each patient was assessed by a chest physician. A standard and comprehensive questionnaire was completed. In addition lung function was assessed by spirometry, and throat and sputum cultures were taken.

For every acute upper or lower respiratory tract infection, an "infection questionnaire" was completed, and sputum was taken for culture. Acute bronchitic episodes were defined as an increase in volume and purulence of sputum, usually associated with an increase in breathlessness, fever, and antibiotic therapy.

Three course of tablets were given at 0, 28 and 56 days. For both placebos and the monobacterial vaccine of the invention, a course consisted of two tablets taken before breakfast each day for 3 consecutive days. For the polybacterial vaccine, each course was given according to the manufacturer's instructions, i.e. 1 tablet day 1, 2 tablets day 2, and 4 tablets day 3. At the completion of the study spirometry was repeated. The only patients lost from the study were those who dies during the trial (Table 1).

Results for the 84 days study period are recorded in Table 2. No significant difference in the incidence of acute upper respiratory tract infection is detected between the 4 groups. However, a significant reduction in both the number of subjects with episode(s) of acute bronchitis (lower respiratory tract infection, $P < 0.005$) and the absolute number of acute bronchitic episodes ($P < 0.002$) is recorded in those subjects given the killed H. influenzae vaccine of the invention. The killed oral H. influenzae vaccine gave a protection a rate of 90 % when compared with the placebo groups, while the polyvalent vaccine gave no protection.

H. influenzae was isolated from 69 % of the sputum samples taken at times of acute bronchitis, compared with an 8 % isolation rate for S. pneumoniae. Bacteriology was performed as usual: Throat swabs and sputum were directly inoculated onto blood agar and chocolate agar plates. H. influenzae isolates were identified by Gram stain, colony morphology in chocolate agar, "satellitism" along a staphylococcus streak on a blood agar plate and dependence of growth on X and V factors. S. pneumoniae isolates were identified by Gram stain, colony morphology and alpha heamolysis on a blood agar plate and optochin sensitivity.

There is no significant correlation between bacteria carriage rate and development of eposides of acute bronchitis. After four weeks of the study colonisation was similar for the subjects taking the placebo and the polybacterial vaccine, but less for the patients treated with the monobacterial vaccine, though the difference did not reach significance. There was a fall in colonisation rate through the following two months in the placebo groups of 28%, the polybacterial vaccine group of 39%, and the monobacterial vaccine group of 56%. However, the trend towards a greater fall in the colonisation rate of the monobacterial vaccine group does not reach significance.

No difference in the pattern of antibody levels could be determined between the four groups. It is surprising that there is no enhancement of saliva antibodies in the case of the polyvalent vaccine, since an increase is known to occur in normal healthy adults. This supports the view that there is a difference in the immune systems of normal healthy patients and those with long term mucosal disease.

uct. The dispensing area, including the freeze drying chamber, are fumigated. Sterile trays, jars and other equipment are used and sterile air is introduced into the chamber at the end of the drying cycle. The weight of $8 \times 10^{13}$ cells lyophilised by this method amounts to 75.8 g ($10^{11}$ cells per 0.1 g).

Tablets are prepared from the lyophilised killed *Haemophilus influenzae* according to the following formula:

| granulation: | lyophilised bacteria | 100 mg |
|---|---|---|
| | sodium taurocholate | 25 mg |

TABLE 1

| | | Patient details | | | | | | |
|---|---|---|---|---|---|---|---|---|
| | | | Sex male/ female | Smoking | | Died during trial | Hospitalised with bronchitis | Forced expiratory volume in one second | |
| | No. | Age | | Never | Current | | | Start of trial | End of trial |
| Placebo 1 | 16 | 65.5 ± 2.9 | 10/6 | 3 | 2 | 0 | 2 | 0.83 | 0.81 |
| Placebo 2 | 17 | 62 ± 2.2 | 16/1 | 2 | 1 | 2 | 5 | 0.94 | 0.99 |
| Polybacterial vaccine Buccalin Berna ® | 17 | 66 ± 1.8 | 15/2 | 2 | 3 | 2 | 1 | 1.05 | 0.93 |
| Monobacterial vaccine of the invention | 17 | 64.7 ± 1.64 | 14/3 | 1 | 2 | 0 | 0 | 1.01 | 1.01 |

TABLE 2

| | Protection induced by oral killed bacterial vaccines | | | |
|---|---|---|---|---|
| | Number of patients with acute infections of: | | Total number of acute lower respiratory tract infections | Isolation of *H. influenzae* in acute lower respiratory tract infections |
| | Upper respiratory tract | Lower respiratory tract | | |
| Placebo 1 | 2/16 | 9/16 | 13 | 12/13 |
| Placebo 2 | 0/17 | 11/17 | 23 | 13/23 |
| Polybacterial vaccine Buccalin Berna ® | 6/17 | 9/17 | 13 | 11/13 |
| Monobacterial vaccine of the invention | 2/17 | 1/17 | 1 | 1/1 |

EXAMPLE

Preparation of a vaccine containing H. influenzae

*Haemophilus influenzae* type B No. 7279 (NIH 1946) is cultured in suspension in a medium of casamino acids essentially as described by P. Anderson, J. Pritt and D. H. Smith, Infection and Immunity 13, 581–589 (1976). The medium consists of 1% Casamino Acids (Difco) 0.5% yeast extract (Difco), 0.05 M sodium phosphate buffer and 0.5% glucose, supplemented with horse blood (dilution (1:1000) and 1 µg/ml nicotinamide adenine dinucleotide (Sigma). This yields approximately $1.3 \times 10^9$ colony-forming units per ml (CPU/ml) and $8 \times 10^{13}$ total viable cells. Similar results are obtained in Eugon broth in place of casamino acids ($7 \times 10^8$ CPU/ml). Cultures are shown to be pure by testing with an api 20B identification kit as well as by microscopic examination. The organisms is notoriously pleomorphic in liquid culture.

Cells are harvested by continuous centrifugation, washed three times using physiological saline and inactivated by resuspending in 0.5% formalin in saline at a concentration of $5 \times 10^9$ CFU/ml. After 3 days, sterility is tested by inoculation into growth media and on CHB agar. No growth of any organism occurs after 7 days incubation at 36° C. Inactivated cells are lyophilised using a protective medium composed of dextran 40/lactose. In the absence of the protective medium, extensive cell disruption is observed. All precautions are taken during lyophilisation to maintain sterility of the prod-

| | lactose | 100 mg |
|---|---|---|
| granulating agent: | alcohol 95SG type F3 | qs |
| dry blend: | maize starch | 10 g |
| | Polyplasdone XL ™ | 7.5 mg |
| | magnesium stearate | 4 mg |

The compression weight is 246.5 mg, showing a core hardness of 5 kg (Monsanto) and a desintegration time of the core in pH 6.8 phosphate buffer of 14 minutes.

The tablets are coated with a coating solution consisting of:

| cellulose acetate phthalate | 12 g |
|---|---|
| propylene glycol | 3 g |
| Tween 80 ® | 1 g |
| alcohol abs. | 40 ml |
| iron oxide red pigment | 0.30 g |
| iron oxide yellow pigment | 1.20 g |
| acetone to | 100 ml |

The enteric coated tablet weighs 265 mg and shows a desintegration time of more than 2 hours in 0.1 N HCl and of 16 minutes in pH 6.8 phosphate buffer.

INDUSTRIAL APPLICABILITY

The vaccine is able to provide improved immunity against acute bacterial infections of the respiratory tract, especially of the bronchi, under circumstances of chronic inflammation; and is particularly valuable for smokers or ex-smokers.

The claims defining the invention are as follows:

1. An enteral non-adjuvenated monobacterial vaccine comprising a killed bacteria for immunization against bacterial infection of mucosal sites;
    the killed bacteria being selected from the group consisting of Haemophilus influenzae, Streptoccoccus pneumoniae, Pseudomonas aeruginosa, and Staphyloccococcus aureus;
    the vaccine comprising a pharmaceutically acceptable carrier which does not elicit an antigenic response and being in the form of an enteric coated tablet, granule, capsule or dragee for oral administration;
    the monobacterial vaccine comprising a single bacteria and being in the absence of any adjuvant therefor, so as to stimulate only a limited immune response in a patient.

2. A method for preventing acute mucosal infections in patients having chronic mucosal disease comprising administering orally to a patient in need thereof, an effective amount of a composition consisting of killed bacteria for immunization against bacterial infection of mucosal sites;
    the killed bacteria being selected from the group consisting of Haemophilus influenzae, Streptococcus pneumoniae, Pseudomonas aeruginosa, and Staphylococcus aureus;
    the vaccine comprising a pharmaceutically acceptable carrier and being in the form of an enteric coated tablet, granule, capsule or dragee for oral administration;
    the monobacterial vaccine comprising a single bacteria and being in the absence of any adjuvant therefor, so as to stimulate only a limited immune response in a patient.

3. The vaccine according to claim 1 in unit dose form and comprising $10^{10}$ to $10^{12}$ bacteria per unit dose.

4. A method of preventing acute mucosal infections in humans having chronic mucosal disease comprising administering, to a patient in need thereof, an effective amount of an enteral non-adjuvenated monobacterial vaccine comprising killing bacteria for immunization against bacterial infection of mucosal sites;
    the killed bacteria being selected from the group consisting of Haemophilus influenzae, Streptococcus pneumoniae, Pseudomonas aeruginosa, and Staphylococcus aureus;
    the vaccine comprising a pharmaceutically acceptable carrier and being in the form of an enteric coated tablet, granule, capsule or dragee for oral administration;
    the monobacterial vaccine comprising a single bacteria and being in the absence of any adjuvant therefor, so as to stimulate only a limited immune response in a patient.

5. The method according to claim 4 wherein acute bacterial infections of the respiratory tract are prevented.

6. The method according to claim 5 wherein acute lower respiratory tract bacterial infections in patients with chronic obstructive lung disease are prevented.

7. The method according to claim 4 wherein one to three unit doses of the vaccine containing $10^{10}$ to $10^{12}$ killed bacteria are administered for two to five consecutive days.

8. The method according to claim 7 wherein the administration for 2–5 days is repeated.

9. The method according to claim 8 wherein the administration course is repeated twice after a three to five week interval.

10. The method, as in claim 4 wherein the vaccine is administered orally.

11. The method, as in claim 4 wherein the chronic mucosal diseases are chronic bronchitis, or cystic fibrosis related disease.

* * * * *